United States Patent [19]

Dexter et al.

[11] 4,383,863
[45] May 17, 1983

[54] 2-[2-HYDROXY-3,5-DI-TERT-OCTYL-PHENYL]-2H-BENZOTRIAZOLE IN STABILIZED PHOTOGRAPHIC COMPOSITIONS

[75] Inventors: Martin Dexter, Briarcliff Manor; Roland A. E. Winter, Armonk, both of N.Y.

[73] Assignee: Ciba-Geigy Corporation, Ardsley, N.Y.

[21] Appl. No.: 241,170

[22] Filed: Mar. 6, 1981

Related U.S. Application Data

[63] Continuation-in-part of Ser. No. 100,400, Dec. 17, 1979, Pat. No. 4,278,590, which is a continuation-in-part of Ser. No. 68,275, Aug. 20, 1979, Pat. No. 4,283,327, which is a continuation of Ser. No. 6,391, Jan. 25, 1979, abandoned.

[51] Int. Cl.³ .......................................... C09H 11/00
[52] U.S. Cl. ................................. 106/125; 548/260
[58] Field of Search ............... 548/257, 260; 106/125

[56] References Cited

U.S. PATENT DOCUMENTS

| | | | |
|---|---|---|---|
| 3,055,896 | 9/1962 | Boyle et al. | 548/260 |
| 3,072,585 | 1/1963 | Millionis et al. | 548/260 |
| 3,074,910 | 1/1963 | Dickson | 548/260 |
| 3,189,615 | 6/1965 | Heller et al. | 548/260 |
| 3,230,194 | 1/1966 | Boyle | 524/91 |
| 3,253,921 | 5/1966 | Sawdey | 430/507 |
| 3,487,453 | 12/1969 | Sheehan | 8/489 |
| 4,041,044 | 8/1977 | White | 260/308 B |
| 4,042,394 | 8/1977 | Smith et al. | 428/207 |
| 4,127,586 | 11/1978 | Rody et al. | 524/91 |
| 4,226,763 | 10/1980 | Dexter et al. | 524/91 |
| 4,230,867 | 10/1980 | Kintopf | 548/260 |

*Primary Examiner*—Theodore Morris
*Attorney, Agent, or Firm*—Luther A. R. Hall; Harry Falber

[57] ABSTRACT

2-[2-Hydroxy-3,5-di-tert-octylphenyl]-2H-benzotriazole exhibits outstanding efficacy in protecting organic substrates from light induced deterioration as well as good resistance to loss by volatilization or exudation during the high temperature processing of stabilized compositions.

This stabilizer and its 5-chloro analog exhibit great resistance to volatilization, enhanced solubility in selected solvents, desirable absorption characteristics in the ultraviolet range and photographic inertness. This combination of properties makes these benzotriazoles particularly useful in photographic compositions especially in protecting color dye images against the harmful effects of ultraviolet light.

9 Claims, No Drawings

2-[2-HYDROXY-3,5-DI-TERT-OCTYLPHENYL]-2H-BENZOTRIAZOLE IN STABILIZED PHOTOGRAPHIC COMPOSITIONS

This is a continuation-in-part of application Ser. No. 100,400, filed Dec. 17, 1979, now U.S. Pat. No. 4,278,590, issued July 14, 1981 which in turn is a continuation-in-part of application Ser. No. 68,275, filed Aug. 20, 1979, now U.S. Pat. No. 4,283,327, issued Aug. 11, 1981 which in turn is a continuation of application Ser. No. 6391, filed Jan. 25, 1979, now abandoned.

BACKGROUND OF THE INVENTION

The present invention pertains to the incorporation of selected 2-aryl-2H-benzotriazoles in photographic products particularly in color photographic compositions to protect color dye images against the harmful effects of ultraviolet radiation.

The UV-absorbers of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 3,004,896; 3,055,896; 3,072,585; 3,074,910; 3,189,615 and 3,230,194.

However the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase compatibility and to reduce volatilization loss by modifying the structure of the benzotriazoles.

In U.S. Pat. No. 3,230,194, a higher alkyl group was substituted for methyl and the latter compound 2-(2-hydroxy-5-tert-octylphenyl)-2H-benzotriazole exhibited superior compatibility and performance in polyethylene compound to former.

Still other attempts were made to increase the compatibility of the aryl-2H-benzotriazole molecules in polymeric substrates and to decrease the tendency of said molecules to volatilize during processing and/or use by substituting the phenolic ring of said compounds with aralkyl groups such as benzyl, α-methylbenzyl and α,α-dimethylbenzyl radicals. Such compounds are disclosed in U.S. Pat. No. 4,127,586; Japanese Kokai No. 158588/75 and U.S. Pat. No. 4,226,763.

Surprisingly, the instant compounds such as 2-(2-hydroxy-3,5-di-tert-octylphenyl)-2H-benzotriazole having only alkyl substitution on the phenolic ring of the benzotriazole exhibit an excellent combination of compatibility with and/or solubility in numerous polymeric substrates along with superior resistance to loss from stabilized compositions during high temperature processing or in end use applications where coatings or films of the stabilized compositions are exposed even to ambient weathering and light exposures compared to stabilized compositions containing the closest 2-aryl-2H-benzotriazoles of the prior art.

In U.S. Pat. No. 4,041,044, an improved process for making 2-aryl-2H-benzotriazoles is taught. In said Specification, a number of phenols and some twelve preferred phenols useful in said process are listed, inter alia 2,4-di-tert-octylphenol. Neither instant compound 2-(2-hydroxy-3,5-di-tert-octylphenyl)-2H-benzotriazole nor 5-chloro-2-(2-hydroxy-3,5-di-tert-octylphenyl)-2H-benzotriazole was exemplified nor prepared in said reference and the outstanding properties of these compounds now seen compared to other prior art benzotriazoles were not then recognized from among the myriad of possible compounds disclosed in this reference.

A dyeable stabilized polymer blend comprising polypropylene, a polyetherester, two phenolic antioxidants, a thiosynergist and 2-(2-hydroxy-3,5-dioctylphenyl)-2,1,3-benzotriazole is disclosed in U.S. Pat. No. 3,487,453. The exact chemical structure of the "dioctyl" substitution on the aryl-2H-benzotriazole moiety is not further identified nor can what influence or effect the benzotriazole exerted in this complex mixture of stabilizers in polypropylene be discerned.

Certain hydrophobic nondiffusing hydroxyphenylbenzotriazoles are disclosed as very useful as ultraviolet light absorbers in photographic gelatin layers (U.S. Pat. No. 3,253,921). The instant benzotriazoles with their great resistance to volatilization, their enhanced solubility in selected solvents, their desirable absorption characteristics in the ultraviolet range and their photographic inertness are particularly useful in photographic compositions, especially in protecting color dye images against the harmful effects of ultraviolet light.

U.S. Pat. No. 3,253,921 discloses benzotriazoles broadly, but does not exemplify the two instant benzotriazoles which are found to be particularly effective in stabilizing photographic compositions against the harmful effects of ultraviolet radiation.

Further background in the area of stabilization of photographic dye images is provided by U.S. Pat. No. 4,042,394 which describes the various components in photographic compositions and the requirements for stabilizing photographic dye images.

DETAILED DISCLOSURE

This invention relates to selected 2-aryl-2H-benzotriazole light absorbers and to photographic compositions stabilized thereby.

More particularly, the 2-aryl-2H-benzotriazoles of this invention are represented by the Formula I

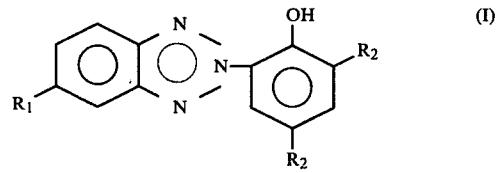

wherein
$R_1$ is hydrogen or chloro, and
$R_2$ is tert-octyl.
Preferably, $R_1$ is hydrogen.
The preferred compound is 2-[2-hydroxy-3,5-di-tert-octylphenyl]-2H-benzotriazole.

Synthesis of Compounds

The compounds of this invention are made by the following procedure:
Step I:

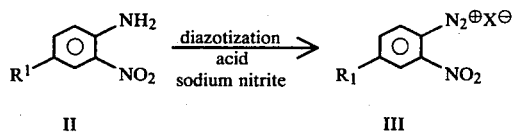

X is an anion such as chloride or sulfate.

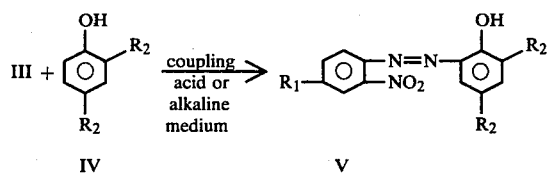

Step II:

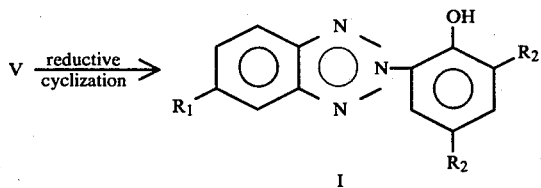

$R_1$ and $R_2$ are as described earlier in the specification.

Step I is the coupling of a diazonium compound with a phenol and can be carried out under either acid or alkaline conditions. Preferably the coupling is carried out under acid conditions to give yields of coupled product, the o-nitroazobenzene intermediate (V) in the range of over 70% of theory.

Step II involves the reductive cyclization of the intermediate V to the corresponding 2-aryl-2H-benzotriazole. This can be conveniently carried out by a number of known reduction methods including zinc and alkali, hydrazine, and catalytic hydrogenation with noble metal or nickel catalysts for this reaction. Good yields of the 2-aryl-2H-benzotriazoles are obtained by using such systems.

The various starting materials, i.e., 2,4-di-tert-octylphenol o-nitroaniline and 5-chloro-2-nitroaniline, are largely available as items of commerce or can easily be prepared by known methods.

A typical photographic composition comprises a paper support on which are coated one or more light-sensitive layers and a layer containing the ultraviolet light absorber in a binder so placed as to protect the layer or layers requiring protection.

It is known that ultraviolet radiation has a detrimental effect on photographic layers. Ultraviolet radiation in light sources used for exposure of photographic products sometimes produces undesired exposure of the layer or layers of a photographic element. This is especially true in photographic elements designed for use in color photography in which the emulsion has been sensitized to the longer wavelength regions and it is desirable to record only the rays of the visible spectrum.

Color photographs on multilayer photographic material, particularly those in which the dye images are formed in sensitive emulsion layers by color development, are susceptible to fading and discoloration by the action of ultraviolet radiation to which the photographs are subjected during viewing. The residual couplers contained in the emulsion layer after the formulation of the picture images may be attacked by ultraviolet radiation resulting in an undersirable stain in the finished photograph. The action of ultraviolet radiation on finished color photographs is particularly noticeable on positive prints on paper or other opaque support since this type of print is frequently viewed in daylight which has a high content of ultraviolet radiation. The dye-fading and discoloration effects appear to be caused primarily by those wavelengths of light close to the visual region of the spectrum, i.e., 300–400 nm.

It is known that silver halide photographic materials can be protected from ultraviolet radiation by incorporating nondiffusing ultraviolet absorbing compounds in the silver halide emulsion layers or in overlying colloid coatings.

A large number of ultraviolet absorbers have been proposed for this use. Ultraviolet absorbing compounds for photograhic use must generally be colorless or nearly colorless, show good compatability with the medium in which they are incorporated, be inert to other photographic addenda in the element and in the processing solution, must have good ultraviolet absorptivity and be stable to ultraviolet radiation. Representative compounds for incorporation in photographic elements are described for example, in U.S. Pat. No. 3,253,921.

Aromatic organic compounds such as ultraviolet absorbers, dye-forming couplers, antistain agents, filter dyes and the like to be effective must be nondiffusing and adequately distributed in highly dispersed form in the aqueous photographic gelatin layers.

This can be accomplished by a variety of chemical or physical techniques including the substitution of sulfonic acid or other solubilizing groups on the organic molecule; by one of a polar organic solvent imbibition procedures; or by solvent dispersion techniques.

The instant 2-aryl-2H-benzotriazoles are extremely useful as ultraviolet absorbers in photographic gelatin layers.

The 2-(2-hydroxy-3,5-di-tert-octylphenyl)-2H-benzotriazole exhibit desirable absorption characteristics in the ultraviolet region, i.e., maximum absorption in the near ultraviolet and sharp cut-off just outside the visible region, is essentially colorless, is readily dispersed or dissolved by either the solvent-dispersion or imbibition methods, and is photographically inert.

Indeed, the 5-chloro-2-(2-hydroxy-3,5-di-tert-octylphenyl)-2H-benzotriazole has the ability to absorb light beyond 400 nm to about 420 nm with a sharp cutoff at the higher wavelength while also possessing the requisite compatibility and other desirable properties mentioned above.

It is contemplated that the use of mixtures of these two instant benzotriazoles in various photographic compositions would give particularly salubrious results.

The instant compounds exhibit excellent compatibility characteristics in the gelatin layers of the photographic composition which lead to compositions essentially without haze coupled with superior protection of the color dye images against the harmful effects of ultraviolet radiation. This combination of properties clearly distinguishes the two instant benzotriazole light absorbers from the generic disclosure of U.S. Pat. No. 3,253,921. These salubrious results are obtained when the instant benzotriazoles are incorporated into the gelatin layer by the solvent dispersion technique.

An object of the invention is to provide novel photographic elements protected against the harmful effects of ultraviolet radiation by incorporation of ultraviolet absorbing materials. Another object is to provide photographic color materials containing ultraviolet absorbers incorporated in a highly stable form. A further object is to provide a nondiffusing ultraviolet absorber. Other objects will become apparent from a consideration of the following specification and claims.

According to the invention, these and other objects are accomplished by the use of the solvent dispersion technique to incorporate in aqueous hydrophilic colloid solutions for coating silver halide emulsion layers or associated hydrophilic colloid layers, an ultraviolet-radiation absorbing compound represented by Formula I:

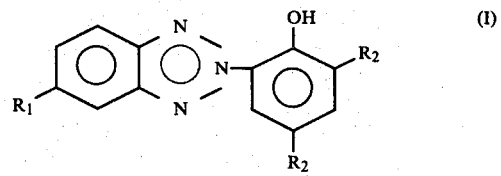

wherein
$R_1$ is hydrogen or chloro, and
$R_2$ is tert-octyl.

An alternative procedure contemplated to incorporate the instant benzotriazoles into a hydrophilic colloid involves heating an aqueous solution of said hydrophilic colloid containing the undissolved benzotriazole and an appropriate dispersing agent to a temperature above the melting point of the instant benzotriazole, agitating the resulting mixture to obtain a fine dispersion of the benzotriazole in the colloid, and then cooling the mixture.

The instant benzotriazole compounds are non-diffusing and have the solubility characteristics needed to carry out the instant invention appropriately.

The compounds of Formula I are incorporated in solvent dispersion advantageously by dissolving them in either a high boiling water-immiscible organic solvent, a low boiling organic solvent, or a water-soluble organic solvent, or in a mixture of a high boiling water-immiscible organic solvent and/or a low boiling and/or water-soluble organic solvent.

The preferred high-boiling solvents include di-n-butyl phthalate, benzyl phthalate, triphenyl phosphate, tri-o-cresyl phosphate, diphenyl mono-p-tert-butylphenyl phosphate, monophenyl di-p-tert-butylphenyl phosphate, diphenyl mono-o-chlorophenyl phosphate, monophenyl di-o-chlorophenyl phosphate, tri-p-tert-butylphenyl phosphate, tri-o-phenylphenyl phosphate, di-p-tert-butylphenyl mono(5-tert-butyl-2-phenylphenyl)phosphate, etc.

The low boiling or water-soluble organic solvents can be used to advantage with or in place of a high boiling solvent. The organic solvents include:

(1) Low boiling substantially water-insoluble organic solvents, such as methyl, ethyl, propyl and butyl acetates, isopropyl acetate, ethyl propionate, sec-butyl alcohol, ethyl formate, butyl formate, nitromethane, nitroethane, carbon tetrachloride, chloroform, etc. and (2) Water-soluble organic solvents, such as methyl isobutyl ketone, 2-ethoxyethyl acetate, 2-butoxy-2-ethoxy-ethyl acetate, tetrahydrofurfuryl adipate, Carbitol acetate (diethylene glycol monoacetate), methoxy triglycol acetate, methyl Cellosolve acetate, acetonyl acetone, diacetone alcohol, butyl Carbitol, butyl Cellosolve, methyl Carbitol, methyl Cellosolve, ethylene glycol, diethylene glycol, di-propylene glycol, acetone, methanol, ethanol, acetonitrile, dimethylformamide, dioxane, etc.

Any water present in the solvent solution must be low enough not to affect adversely the solubility of the absorber.

The low boiling or water-soluble solvents may be removed from the dispersion, for example, by air-driving a chilled, noodled dispersion or by continuous water-washing.

The ultraviolet absorbing layer is coated from a composition comprising a solvent dispersion of a compound of Formula I made by dissolving the compound in an organic solvent and dispersing this solution in an aqueous solution of a hydrophilic colloid or binder.

Binders that are particularly advantageous to use include gelatin, albumin, etc., cellulose derivatives, polyvinyl compounds, etc. The polymeric binders include polyvinyl alcohol or a hydrolyzed polyvinyl acetate; a far hydrolyzed cellulose ester such as cellulose acetate hydrolyzed to an acetyl content of 19–26 percent; a water-soluble ethanolamine cellulose acetate, a polyacrylamide having a combined acrylamide content of 30–60 percent and a specific viscosity of 0.25–1.5 on an imidized polyacrylamide of like acrylamide content and viscosity; a vinyl alcohol polymer containing urethane carboxylic acid groups of the type; or containing cyanoethyl groups such as the vinyl alcohol-vinyl cyano-acetate copolymer; or a polymeric material which results from polymerizing a protein or a saturated acylated protein with a monomer having a vinyl group.

The dispersion of an absorbing compound of Formula I in the binder material is coated over the light-sensitive layer of the photographic element. Where the photographic element is a material intended for use in color photography, the ultraviolet filter layer need not be an outer layer, but can be used as an interlayer, i.e., under the layer or layers not needing the protection and over the layer or layers needing protection. For example, in a multilayer material comprising three differentially sensitized layers, the red-sensitive layer being adjacent to the support, the green-sensitive layer being superimposed on the red-sensitive layer and the blue-sensitive layer being outermost with respect to the other light-sensitive layers, the ultraviolet filter layer can be placed between the blue and green-sensitive layers or between the green and red-sensitive layers. Similarly, in another photographic element in which the layers are reversed, that is, the blue-sensitive layer is coated over the support, and the green and red-sensitive layers are superposed over the blue-sensitive layer in that order, the ultraviolet filter layer can be over all three layers or between any two of the layers. Alternatively, the ultraviolet absorbing composition can be incorporated directly in the light-sensitive emulsion instead of, or in addition, being present in another layer. The amount of the ultraviolet absorbing material used can be varied, depending upon the effect desired and the use that will be made of the material.

The ultraviolet absorbing compositions are coated over a wide range of concentrations; usually they are coated in the range of from 20 to 300 mg. of ultraviolet absorbing compound per ft.$^2$ photographic element. A preferred range is from 75 to 160 mg/ft.$^2$. The optimum coating concentrations will depend upon the particular photographic element to be protected and the amount of protection desired. The optimum coating concentrations for a given photographic element can be determined by methods well known in the art.

Any photographic element may be advantageously protected according to the invention. These photographic elements may have as their support any of the conventional support materials, such as firm supports, e.g., cellulose acetate, etc. opaque supports, such as white pigmented film, paper and the like.

The ultraviolet absorbing compounds of Formula I are characterized by their nondiffusibility in coated layers, good stability in the incorporating solvents and their good ultraviolet absorption. Ultraviolet absorbing layers containing compounds of Formula I incorporated according to the preferred methods of the invention have unexpectedly excellent stability upon prolonged exposure to ultraviolet radiation which makes them ideally suited for protecting photographic elements, particularly dye images in color materials.

The amount of solvent to be retained in the final coating made according to my invention can be adjusted according to the requirements of the product and by selecting solvents or a mixture of solvents of appropriate volatility and/or water solubility.

The following examples are presented for the purpose of illustrated only and are not to be construed to limit the nature of scope of the instant invention in any manner whatsoever.

EXAMPLE 1

2-Nitro-2'-hydroxy-3',5'-di-tert-octylazobenzene

To a 5-liter, 3-necked flask fitted with a stirrer and thermometer was charged 317.3 grams of a 26% aqueous solution of technical naphthalenesulfonic acid, 6.7 grams of Triton X-207 (non-ionic surfactant), 19.6 grams of Conco AAS-90F (sodium dodecylbenzenesulfonate) and 315 ml of water. The mixture was warmed to 40° C. and then 393.6 grams of 2,4-di-tert-octylphenol was slowly added to the mixture with vigorous stirring keeping the temperature at 40° C.

A cold solution of o-nitroaniline diazonium chloride, prepared from 174.3 grams (1.26 mole) of o-nitroaniline and 87.1 grams (1.26 mole) of sodium nitrite in concentrated aqueous hydrochloric acid solution at a temperature of $-5°$ to $0°$ C., was added dropwise into the reaction mixture over a 1.5-hour period. The resulting deep red to black reaction mixture was kept at 40° C. overnight. The temperature was raised to 65° C. for 1 hour; then the 95° C. for another 30 minutes. After cooling to 35° C., the reaction mixture was isolated as a fine dark red solid by filtration.

The crude product was triturated with 3.5 liters of water; then with 1400 ml of methanol and stirred in a blender, and filtered to yield a fine granular product. The dark red o-nitroazobenzene intermediate named above was obtained in a yield of 419.7 grams (72.7% of theory) and melted at 110°-112° C. Thin layer chromatography indicated a homogeneous product.

EXAMPLE 2

2-(2-Hydroxy-3,5-di-tert-octylphenyl)-2H-benzotriazole

To a 5-liter 3-necked flask fitted with a stirrer, thermometer, reflux condenser and nitrogen inlet was charged 400 grams (0.855 mol) of the o-nitroazobenzene intermediate of Example 1 and 1200 ml of toluene. To the resulting solution was added 260 ml of isopropanol and 260 ml of water. A nitrogen atmosphere was imposed and 175 ml of 50.1% aqueous sodium hydroxide was added. A flask containing 170.0 gram (2.6 gramatoms) of zinc was connected to the reaction flask by Gooch rubber tubing and the zinc dust was added portionwise to the reaction mixture over a 120-minute period. The zinc was added at such a rate to keep the internal temperature at 70° C. After the zinc was all added, an additional 30 ml of 50.1% sodium hydroxide and 20 grams of zinc were added to insure complete reaction. The reaction mixture was heated for 3 hours at 70° C. The mixture was cooled to room temperature by standing overnight and acidified with 500 ml of concentrated hydrochloric acid.

The zinc sludge was removed by filtration. The product was contained in the organic layer, which was washed with three 1000 ml portions of water, then 500 ml of saturated salt solution, and then dried over anhydrous sodium sulfate. The organic solvent was removed in vacuo to yield a crude product as a viscous syrup which crystallized on standing.

The crude product was recrystallized twice from 1000-1100 ml of ethanol to give 253 grams (67.8% of theory) of a pale yellow solid melting at 105°-106° C. of the above named compound. (Compound 1).

Analysis: Calcd for $C_{28}H_{41}N_3O$: C: 77.20; H,9.49; N:9.65. Found C: 77.22; H,9.14; N:9.77.

EXAMPLE 3

4-Chloro-2-nitro-2'-hydroxy-3',5'-di-tert-octylazobenzene

Coupling of 2,4-di-tert-octylphenyl with diazotized 4-chloro-2-nitroaniline using the procedure of Example 1 furnished the above-named compound as a deep red solid in 61.6% yield.

EXAMPLE 4

5-Chloro-2-(2-hydroxy-3,5-di-tert-octylphenyl)-2H-benzotriazole

When, using the general procedure of Example 2, the amount of 4-chloro-2-nitro-2'-hydroxy-3',5'-di-tert-octylazobenzene was substituted for 2-nitro-2'-hydroxy-3',5'-di-tert-octylazobenzene, the abovenamed compound was prepared in a yield of 71.8% as pale yellow crystals melting at 121°-122° C. (Compound 2)

Analysis: Calcd for $C_{28}H_{40}ClN_3O$: C: 71.54; H,8.58; N:8.94. Found C: 71.26; H,8.46; N:9.03.

EXAMPLE 5

Haze Development in Photographic Compositions

The direct assessment of the compatibility of benzotriazole light stabilizers in photographic compositions is difficult. The compositions containing such stabilizers in photographic oils often take extended periods of time for separation or haze to be observed.

An important property of photographic compositions directly related to such compatibility parameters related to such compatibility parameters is haze. For the preparation of clear and precise preparation of clear and precise photographic images, haze must obviously be minimized or better yet essentially eliminated. The measurement of light scattering properties as described below is directly correlative to haze measurements in the photographic compositions.

To a solution of 200 mg of gelatine, 2 mg of Nekal BX (an anionic wetting agent) and 10 mg of hardener A

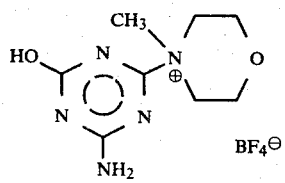

in 8.5 ml of water was added a solution of 0.05 millimole of the benzotriazole UV absorber and different quantities of tricresyl phosphate (TCP) or dibutyl phthalate (DBP) in 0.5 ml of ethyl acetate.

A very fine dispersion of the organic phase was produced by ultrasonic mixing (5 min./120 W). This dispersion was coated onto a glass plate of 13×18 cm. The coatings were dried and hardened for 3 days at room temperature (20° to 22° C.) and then subjected to the following treatments:

Treatment A: 4 days at room temperature (20° to 22° C.)
Treatment B: 7 days at 43° C./60% relative humidity
Treatment C: 7 days at 4° C.

The optical densities of the coatings were measured at 500 nm and 600 nm and from the values obtrained the so called "β-values" were calculated (see M. B. Huglin, Light Scattering from Polymer Solutions, p. 375–379, Academic Press 1972).

$$\beta = 4 - \frac{\log \frac{D\,500}{D\,600}}{0.079}$$

The β-value is a measure of the light scattering properties of a solution or a layer. For a UV-protecting layer in a photographic material the β-value should be as high as possible since scattering will decrease the sharpness in underlying layers and cause a haze on the final material. In the following table β-values are given for Compound 1 of the instant invention and for some commercial benzotriazole UV absorbers.

TABLE 1

| | Treatment | | | | | | | | | |
|---|---|---|---|---|---|---|---|---|---|---|
| | A | | | | B | | | | C | |
| | TCP | | DBP | | TCP | | DBP | | DBP | |
| | 1:1[1] | 1:3[1] | 1:1 | 1:3 | 1:1 | 1:3 | 1:1 | 1:3 | 1:1 | 1:3 |
| Compound No. 1 | 2.94 | 2.98 | 3.33 | 3.03 | 2.86 | 2.88 | 3.15 | 2.97 | 3.17 | 2.83 |
| UV absorber A | 2.55 | 2.53 | 2.92 | 2.70 | 2.53 | 2.46 | 2.97 | 2.63 | 2.60 | 2.49 |
| UV absorber B | 2.52 | 2.37 | 2.85 | 2.54 | 2.35 | 2.32 | 2.80 | 2.37 | 2.77 | 2.46 |
| UV absorber C | 2.59 | 2.14 | 2.52 | 2.47 | 2.54 | 2.39 | 2.64 | 2.21 | 2.57 | 2.29 |

[1] solvent-to-UV absorber ratio (gram per gram)

UV absorber A: 2-(2-hydroxy-3,5-di-tert-amylphenyl)-2H-benzotriazole
UV absorber B: 2-(2-hydroxy-3-sec-butyl-5-tert-butylphenyl)-2H-benzotriazole
UV absorber C: 2-(2-hydroxy-5-tert-octylphenyl)-2H-benzotriazole The β-value figures in the table clearly demonstrate in every case that layers containing Compound 1 of this invention have higher transparency than those which contain benzotriazole UV absorbers known in the prior art.

Visual inspection of the actual photographic layers on which the β-values were obtained confirms that the layers containing the Compound 1 benzotriazole exhibited essentially no haze while the layers containing the prior art benzotriazoles possessed discernible haze.

EXAMPLE 6

Effectiveness of Benzotriazole UV absorbers in Protecting Color Layer in Photographic Composition In Example 5, it was shown that Compound 1 led to essentially no haze in photographic compositions. This property, however desirable, would not bestow onto Compound 1 practical utility if Compound 1 did not also provide acceptable protection to the color layer in such compositions against the harmful effects of ultraviolet light.

Photographic composition were prepared as follows:
1. Coupler emulsion:
38.9 mg of Coupler A

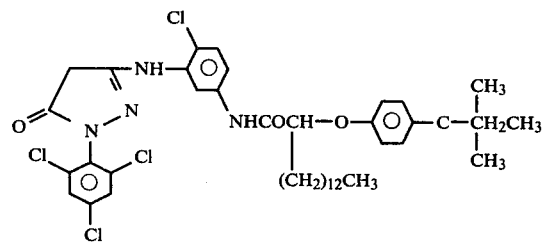

and 100 mg of tricresyl phosphate are dissolved in 1 ml of methylene chloride, part of the solvent is evaporated and to the rest is added a solution of 480 mg of gelatin and 40 mg of Nekal BX (anionic wetting agent) in 9.9 ml of water. A very fine dispersion of the organic phase is produced by ultrasonic mixing (10 min./120 W).

2. Light-sensitive layer:

To 2.5 ml of the coupler emulsion were added: 4.5 ml of water and 2 ml of a silver bromide emulsion (55 g silver and 70 g gelatine per kg). The whole was well mixed, then coated onto a piece of opaque triacetate film of 13×18 cm and the coating is dried 24 hours at room temperature.

3. Protecting layer:

To a solution of 200 mg of gelatine, 2 mg of Nekal BX and 20 mg of hardener A (see structure in Example 5) in 9 ml of water is added a solution of 0.05 millimole of the UV absorber and 330 mg of dibutyl phthalate per g of benzotriazole UV absorber in 0.5 ml of ethyl acetate.

A very fine dispersion of the organic phase is obtained by ultrasonic mixing (5 min./120 W). This dispersion is coated in the dark onto the light-sensitive layer. The material is then dried 7 days at 20° C. and then exposed through a step wedge (0.15 log E difference per step). The material is then processed in the Kodak E+2 process and half of the strip exposed in a Atlas Weather-Ometer with a total of 5000 Langley (21 kWs/cm²). The loss of dye density is measured on the two steps which are closest to a remission density of 1. Table 2 contain the values for the different UV absorbers.

TABLE 2

| | Loss of dye density in percent at $D_r = 1.0$ |
|---|---|
| Control (no UV absorber) | 90 |
| Compound 1 | 41 |
| UV absorber A | 47 |
| UV absorber B | 56 |
| UV absorber C | 50 |

(see footnote, Table 1, Example 5 for structures of A, B and C)

These figures clearly demonstrate that the instant Compound 1 gives surprisingly better protection than other benzotriazole UV absorbers to the dye in the color layer of a photographic composition.

What is claimed is:

1. An ultraviolet absorbing dispersion comprising a gelatin binder material and a hydrophobic compound selected from those having the formula:

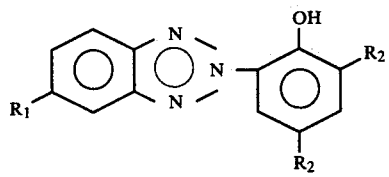

wherein $R_1$ is hydrogen or chloro, and $R_2$ is tert-octyl.

2. An ultraviolet absorbing dispersion comprising a gelatin binder material, a solvent and a hydrophobic compound selected from those having the formula:

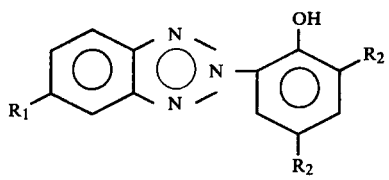

wherein $R_1$ is hydrogen or chloro, and $R_2$ is tert-octyl.

3. An ultraviolet absorbing dispersion of claim 1 in which said solvent is high boiling water-immiscible organic solvent.

4. An ultraviolet absorbing dispersion of claim 1 in which said solvent is a water miscible organic solvent.

5. An ultraviolet absorbing dispersion of claim 1 in which said solvent is a low boiling organic solvent.

6. An ultraviolet absorbing dispersion of claim 1 in which said solvent is a mixture of a high boiling water-immiscible organic solvent and a low boiling or water-soluble organic solvent.

7. An ultraviolet absorbing layer for photographic elements coated from a dispersion of claim 2.

8. As aqueous gelatin coating composition comprising a dispersion of water, gelatin and an ultraviolet absorbing hydrophobic compound selected from those having the formula:

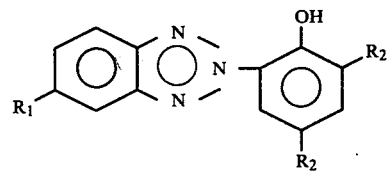

wherein $R_1$ is hydrogen or chloro, and $R_2$ is tert-octyl.

9. An aqueous gelatin coating composition of claim 8 containing an organic solvent for said ultraviolet absorbing compound.

* * * * *